United States Patent [19]

Cole

[11] 4,389,575

[45] Jun. 21, 1983

[54] FABRIC INSPECTION SYSTEM

[75] Inventor: Frederick A. Cole, Jackson, Mich.

[73] Assignee: Sparton Corporation, Jackson, Mich.

[21] Appl. No.: 165,780

[22] Filed: Jul. 3, 1980

[51] Int. Cl.³ ............................................. G01N 21/88
[52] U.S. Cl. ..................................... 250/563; 356/430
[58] Field of Search .............. 250/562, 563, 571, 572, 250/214 R, 559; 356/429, 430, 431

[56] References Cited

U.S. PATENT DOCUMENTS

| | | | |
|---|---|---|---|
| 3,560,096 | 2/1971 | Watson et al. | 250/563 |
| 3,729,635 | 4/1973 | Shottenfeld et al. | 250/562 |
| 3,795,452 | 3/1974 | Bourdelais et al. | 250/563 |
| 3,812,373 | 5/1974 | Hosoe et al. | 250/562 |
| 3,994,586 | 11/1976 | Sharkins et al. | 356/73 |
| 4,075,498 | 2/1978 | Takasuka et al. | 250/572 |
| 4,103,177 | 7/1978 | Sanford et al. | 250/572 |
| 4,207,472 | 6/1980 | Idelsohn et al. | 250/563 |

*Primary Examiner*—David C. Nelms
*Attorney, Agent, or Firm*—Beaman & Beaman

[57] ABSTRACT

A system for electronically inspecting fabric for defects wherein a moving fabric is scanned by light sensing apparatus for variations in light reflecting characteristics due to the presence of a defect. The sensitivity of the system is monitored by an automatic background control circuit to adapt the system to the light reflective characteristics of the particular fabric being inspected and alarm and defect counting apparatus indicates and records the presence of a defect. The system permits the inspection to be terminated upon the detection of a defect, or alternatively, the quality of the fabric can be determined by recording spaced defects during successive defect recordable time periods, the duration of such time periods being adjustable.

5 Claims, 3 Drawing Figures

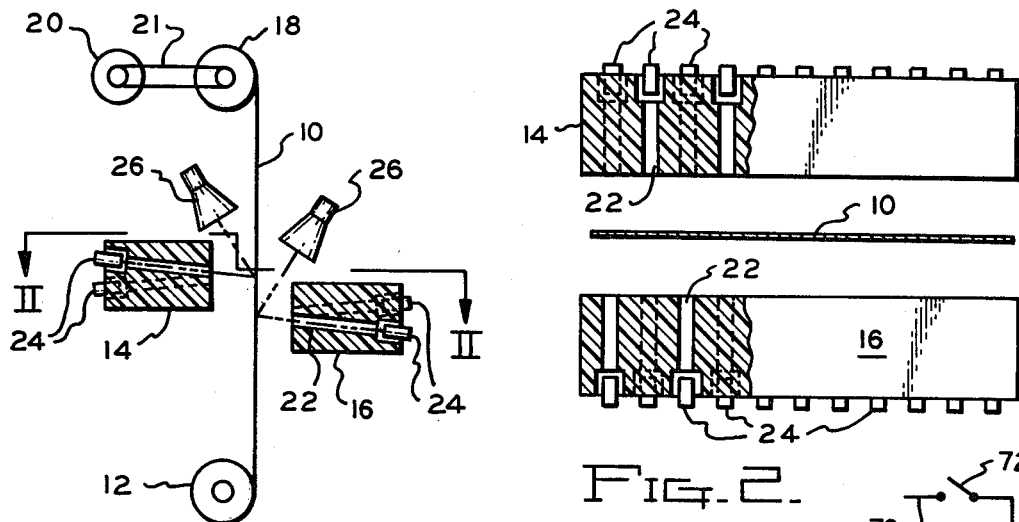
Fig. 1.
Fig. 2.
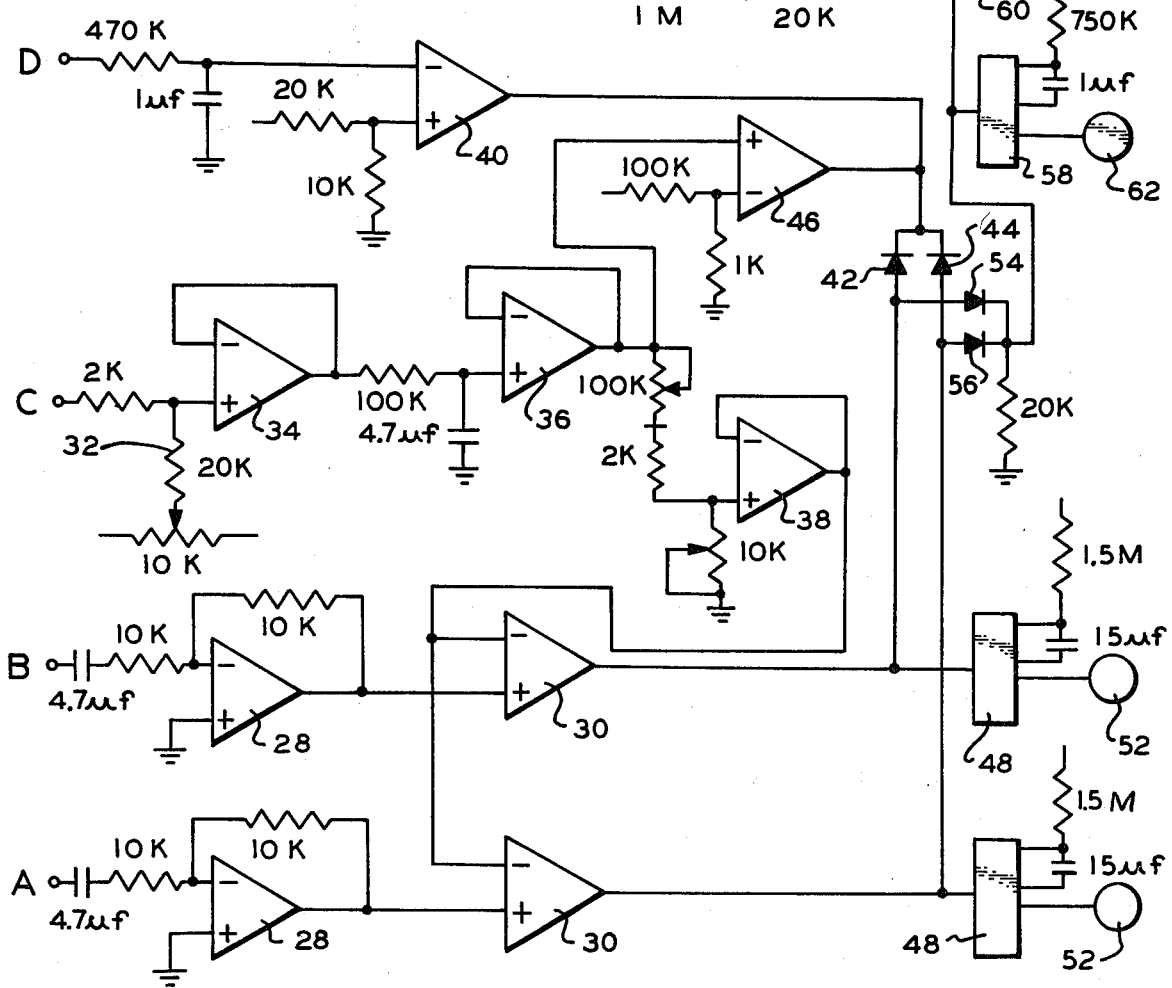
Fig. 3.

FABRIC INSPECTION SYSTEM

BACKGROUND OF THE INVENTION

In the textile art the fabric produced is inspected for defects which may occur due to missed stitches apparatus malfunctioning, broken needles, snagging or other causes, and the quality and price of a fabric is affected by the number of defects per unit of fabric length.

Fabric inspection is usually by the human eye, and such manual observation is inconsistent due to human factors such as fatigue, momentary distraction, light variations, and difficulty in observing defects existing in rapidly moving material.

Automatic defect detection apparatus for fabrics has been developed and such devices often use light reflection systems for scanning the fabric face such as shown in U.S. Pat. Nos. 3,160,759; 3,589,816; 3,786,265; 4,057,351; 4,075,498 and 4,103,177.

Prior art light reflection inspection apparatus has been used to terminate the operation of knitting and weaving machines, or to energize an alarm or otherwise indicate the presence of a sensed defect. However, it is not believed that prior art fabric inspection systems of relatively economical manufacture have been capable of recording the number of spaced defects occurring within sequential time intervals whereby the quality of the material may be readily determined, and upon the completion of inspection the fabric readily classified as to its quality.

It is an object of the invention to provide an automatic fabric inspection system which is capable of inspecting flat material moving at high speeds, for instance, inspection speeds to 200 yards per minute are possible and defects as small as 1/16 of an inch diameter may be sensed.

A further object of the invention is to provide a fabric inspection system for flat material wherein inspection may take place on either side of the material, or both sides if a double layered material is being handled.

Another object of the invention is to provide inspection apparatus utilizing reflected light sensors wherein the ability of the fabric to reflect light is automatically sensed and the circuit is automatically adjusted for the light reflective characteristics of the particular fabric being inspected.

Yet another object of the invention is to provide a fabric inspection system utilizing visible and audible alarms wherein the alarms are disabled when the inspection system drive is de-energized, or fabric is not being sensed.

A significant object of the invention is the utilization of a counter in a fabric inspection system which permits the counting of defects only during spaced time intervals wherein an indication of the quality of the fabric is provided.

In the practice of the invention the fabric material being inspected is transferred from one roll to another as a flat web or strip, the "wind up" roll being driven by an electric motor. As the fabric is transferred from the take off roll to the wind up roll defect sensing heads located upon both sides of the fabric and disposed adjacent thereto electronically scan the material throughout its width. The sensing apparatus includes an infrared light source illuminating the portion of the fabric which is scanned by a plurality of infrared sensitive light detectors. The light detectors receive the reflected light from the fabric, and upon a defect occurring a variation in the light reflective characteristics will momentarily occur which will produce a variation in the electronic signal produced by the detector, and this signal is amplified within the circuit of the invention to energize alarms, actuate a counter, or de-energize the wind up roll motor.

The circuit of the invention includes an automatic background sensing control, and means for sensing operation of the wind up roll motor. Upon the motor being de-energized, or the background control sensing the absence of fabric, the circuit is disabled whereby new material may be threaded into the inspection apparatus without triggering the alarms and counter of the system.

Upon the sensing of a defect the resulting electronic signal energizes visual and audible alarms, and also produces an electronic pulse which advances a defect counter. Additionally, the defect signal is imposed upon a relay selectively connectable to the control for the wind up roll motor. The duration of the pulse which operates the counter is adjustable, and during the duration of the counter energizing pulse the occurrence of additional defects are not recorded on the counter. Thus, the counter only records those defects which are spaced from each other by a predetermined distance as regulated by the adjustment of the counter pulse duration, permitting the operator to determine the quality of the fabric being inspected throughout its length. Thus, it is possible to determine how much of the fabric on a roll is usable and defect free. Defects which are adjacent each other do not require the discarding of as much fabric as when the defects are widely spaced on the web and by recording only spaced defects the roll quality is ascertained.

The defect controlled relay connected to the winding roll motor may be selectively abled and disabled whereby the presence of a defect may selectively stop the motor and inspection, or the relay may be rendered ineffective to control the winding roll motor. When the quality of the fabric is to be determined by the counter, and the number of defects occurring between counter actuating pulses, the motor relay is disabled with respect to control over motor operation.

BRIEF DESCRIPTION OF THE DRAWINGS

The aforementioned objects and advantages of the invention will be appreciated from the following description and accompanying drawings wherein FIG. 1 is a schematic representation of a fabric inspection system in accord with the invention, FIG. 2 is a top plan view, partially sectioned, of the inspection heads as taken along Section II—II of FIG. 1, and FIG. 3 is a circuit diagram illustrating the basic components of the circuit of the fabric testing system of the invention.

DESCRIPTION OF THE PREFERRED EMBODIMENT

In FIG. 1 a schematic description is illustrated as to the relationship of components employed in the fabric inspection system of the invention. The fabric 10 to be inspected is located upon a roll or spool 12 constituting a dispensing roll or take off roll, and initially the end of the fabric is inserted between inspection heads 14 and 16 and attached to the take up roll 18. The take up roll 18 is rotated in a counterclockwise direction by an electric motor 20 connected to the take up roll or spool by a belt 21. In actual practice, the path of movement of the fabric 10 may be considerably more complex than that shown in FIG. 1, wherein a plurality of rollers may be located between the dispensing and take up rolls and the fabric may change directions several times intermediate the rolls.

The fabric 10 comprises a flat material, as will be appreciated from FIG. 2, and may either be a single layer, or a double layer, as is often produced by tube knitting machines. By using two sensing heads 14 and 16 both faces of the material may be simultaneously inspected if the material comprises a double layer. However, only a single sensing head need be employed in the practice of the invention.

The inspection heads 14 and 16 each constitute a block having a plurality of light receiving passages 22 located therein and alternate passages are obliquely related to each other in a vertical plane wherein the passages may be closely oriented. The inner ends of the passages intersect the associated block end for receiving light reflected from the adjacent fabric face, and the outer end of each passage is provided with an electronic light detector 24 constituting a photo transistor having uniform electrical conducting characteristics as long as the amount of light entering the detector is uniform. An infrared light source 26 is disposed adjacent each sensing head illuminating the fabric face adjacent the inner end of the passages 22, and the detectors 24 are sensitive to the reflected infrared light received within the associated passage. The detectors 24 of each sensing head are connected in parallel, and the passages are so related and disposed adjacent the fabric face that a continuous "slot" the width of the fabric material 10 is being sensed.

The construction of the sensing heads 14 and 16 does not constitute an aspect of the instant invention, and the sensing heads are described in greater detail in my co-pending U.S. patent application Ser. No. 90,335 filed Nov. 1, 1979, now U.S. Pat. No. 4,249,081. Other types of electronic defect sensing heads could be employed with the circuit of the invention wherein an electronic signal is produced upon the sensing of a defect in the fabric material.

The circuit employed with the invention is illustrated in FIG. 3, and described below:

Input into the circuit is represented at terminals A and B which constitute the outputs of the sensing heads 14 and 16, respectively. Terminal C receives the output of the automatic background control sensor which is usually mounted into a sensing head 14 or 16 and may comprise a photo transistor similar to 24 which transmits a voltage to terminal C proportional to the amount of infrared light being reflected from the fabric. The fourth input into the circuit is at terminal D which is connected to the electrical circuit of the motor 20 wherein an output is provided at D when the motor 20 is energized.

As the circuits associated with inputs A and B are identical the description of one suffices for both, and from FIG. 3 it will be appreciated that 28 is an integrated circuit inverting amplifier with AC coupling on the input with a gain of minus one wherein the polarity is opposite to that of which was introduced into the amplifier. Thus, upon a defect being sensed a positive signal is generated and amplified as an output of the integrated circuit 28. The output of the operational amplifiers 28 is fed to integrated circuit comparators 30 which are also receiving a comparative voltage at the minus input which comes from the automatic background circuit originating at terminal C.

The input at terminal C may include a slight DC offset voltage when no light is being sensed and resistor 32 removes this DC offset in order to "zero" the circuit from a dark condition. Integrated circuit 34 is a noninverting amplifier. The 100 K resistor and 4.7 uf condenser filter the output of the integrated circuit 34 to produce a clean direct current voltage wherein the noise has been removed from the background control signal. The integrated circuit 36 is a unity gain noninverting buffer and the output of integrated circuit 36 is fed to a voltage divider network, and a portion of the DC output voltage at integrated circuit 36 is used to produce a voltage reference signal to be imposed upon the circuits associated with the sensing heads. The 10 K variable resistor is adjustable by the operator to take out the noise or background, but yet render the circuit sensitive to the presence of a defect. Variable resistance 100 K is factory adjusted to limit the maximum voltage that the operator could achieve by adjustment of the 10 K resistor. The output of the voltage regulator is connected to the positive input of the integrated circuit 38, whose output is connected to the integrated circuit voltage comparators 30 at the negative terminal, and in this manner the signals received from the sensing heads can be compared to the background control voltage which will vary in accordance with the reflectivity of the particular fabric being sensed, and/or the lamp intensity.

The voltage input at terminal D is from a relay coil, not shown, associated with the control for motor 20, and this voltage would only be present when the motor is energized. This voltage goes to ground, but a delay is achieved by the 470 K resistor and the 1 uf condenser, as well as the voltage divider at the positive input of integrated circuit 40. The output of the integrated circuit 40 is connected to diodes 42 and 44, associated with the output of the comparators 30 associated with sensing heads 14 and 16, and the diodes function to enable and disable the alarm and counter functions of the circuit, as later described.

A portion of the output of integrated circuit 36 as determined by the input at the automatic background control terminal C is introduced to the positive terminal of integrated circuit 46 which has a voltage divider network associated with the negative input thereof. The output of integrated circuit 46 is also connected to diodes 42 and 44, and it will therefore be appreciated that these diodes are capable of being turned on by the voltage at the automatic background control input C, or the motor sensing terminal D which will disable the alarm circuits.

The output of the comparators 30 is normally low, and upon the sensing of a defect the output becomes high for the duration of the defect. This pulse is supplied to the "one shot" integrated circuits 48. Activation of integrated circuits 48 produces a pulse which will illuminate the associated alarm indicator lamp 52, and the duration of the energization of the associated lamp is determined by the value of the resistor and condenser associated with the integrated circuit 48. In the commercial embodiment of the invention the lamp will stay energized for seven seconds upon indication of a defect.

The high signals at comparators 30 will also be conducted to diodes 54 and 56 which constitute an "or"

circuit wherein this high signal is transmitted to the integrated circuits 58 and 60. The integrated circuit 58 is connected to an audible sound generator 62 which will produce an audible signal for a duration as determined by the 750 K resistor and 1 uf condenser, this signal usually lasts less than ½ second.

The defect signal is also transmitted to integrated circuit 60 which has an output connected to a counter or totalizer 64, and a relay coil 66. The duration of the pulse to the counter 64 is determined by the 6.8 uf condenser, the 20 K resistor, and resistor 68 of a 1 M ohm value, which is adjustable, and will vary the duration of the pulse to the counter.

The counter 64 is operated once by each pulse received from integrated circuit 60, and if another defect signal is received by the circuit during the duration of the pulse operating counter 64 such defect signal will not affect the counter in that reception by the counter will be blocked by the ongoing pulse. Upon the counter pulse terminating the circuit to the counter is again capable of accepting a defect signal and will count the same. Accordingly, the counter 64 will register only those defects received intermediate its actuating pulses, and the counter will register only those defects which are spaced apart on the fabric a sufficient distance to permit the pulse duration to terminate for accepting and recording a new defect signal. The duration of the counter pulse will be adjusted in accord with the rate of translation of the fabric being inspected and the spacing desired between recordable defects, and it is thereby possible to determine the quality of the fabric being inspected with respect to the occurrence of spaced defects.

The relay 66 includes contacts associated with conductor 70, and this conductor includes a switch 72. The conductor 70 is connected to the controls for motor 20 whereby, upon switch 72 being closed, the motor will stop upon a defect being sensed. Thus, when switch 72 is closed the inspection operation will automatically terminate upon each defect being sensed, and no counting of the defects takes place. The switch 72 will be open when it is desired to determine the quality of the fabric, rather than terminate inspection at the occurrence of each defect, and this selective operation of the circuit permits the operator flexibility of operation. For instance, if the operator desires to mark the location of each defect the switch 72 will be closed, and in those instances where the location of the defect is not of prime importance, but the number of defects within a fabric strip at spaced locations is significant, the counter 64 and pulse adjustment is employed.

The integrated circuits and diodes illustrated are commercially available, and in the following schedule the components are identified by reference numeral, manufacturer and part number.

| Reference | Manufacturer | Part Number |
|---|---|---|
| 28,34,36 | National Semiconductor | LM 324 |
| 30,40,46 | National Semiconductor | LM 339 |
| 38 | National Semiconductor | LM 1458 |
| 48,58,60 | RCA | CD 4098B |
| 42,44,54,56 | — | IN 4148 |

It is appreciated that various modifications to the inventive concepts may be apparent to those skilled in the art without departing from the spirit and scope of the invention. For instance, while the invention is disclosed as a "fabric inspection system" the apparatus is not limited for use with textile fabric, but may be used in those arts such as paper making, rubber and plastic processing, or the like, wherein the inspection of a moving strip or web is desired. Likewise, rather than the material being dispensed from, or wound on, rolls the material may be handled as folded stacks and translated by drive rollers.

I claim:

1. A fabric inspection system wherein relative movement occurs between a fabric and fabric inspection apparatus, comprising, in combination, motor means translating the fabric to be tested past an inspection station, electronic sensing means for detecting a defect in the fabric located at said inspection station and producing an electronic signal upon a defect being sensed, amplifier means amplifying said signal, a counter for recording the occurrence of a defect, counter control means connected to said amplifier means receiving said amplified signal and producing an electric pulse for operating said counter to record a defect wherein each pulse records a single defect upon said counter, said counter control means including pulse duration adjustment means whereby the duration of said pulse may be adjusted, said pulse, during its duration, rendering said counter control means inoperative to operate said counter upon receiving an amplified defect signal whereby said counter records only defect signals received intermediate pulse durations providing a defect count for spaced defects as determined by said pulse duration.

2. In a fabric inspection system as in claim 1, motor control means connected to said amplifier means and operated by an amplified defect signal, and switch means selectively connecting said motor control means to said motor means wherein positioning of said switch means to a first position connects said motor means and motor control means to de-energize said motor means upon a defect signal occurring and positioning of said switch means to a second position renders said motor control means inoperative to control said motor means permitting the counting of defects as determined by said pulse duration.

3. In a fabric inspection system as in claim 1, motor sensing means sensing operation of said motor means producing an electronic signal during motor means operation which maintains the circuit between said counter and amplifier means operative and disables the circuit between said counter and amplifier means upon termination of motor means operation, electronic alarm means connected to said amplifier means, said alarm means comprising a lamp and an audible signal generating means and energized by the occurrence of a defect signal, said motor sensing means disabling the circuit between said amplifier means and alarm means during termination of motor means operation and enabling the circuit between said amplifier means and alarm means during motor means operation.

4. In a fabric inspection system as in claim 1, said electronic sensing means comprising first and second heads mounted on opposite sides of the fabric to be inspected whereby a double faced fabric between said heads is simultaneously inspected on both faces, first and second amplifier means associated with said first and second heads, respectively, and means connecting said counter control means to said first and second amplifying means whereby said electric counter pulse may be initiated from either head.

5. In a fabric inspection system as in claim 4, alarm means connected to each of said amplifier means indicating the occurrence of a defect signal at the respective associated head.

* * * * *